US005908748A

United States Patent [19]
Ma et al.

[11] Patent Number: 5,908,748
[45] Date of Patent: Jun. 1, 1999

[54] SPECIES-SPECIFIC YEAST TFIIB SEQUENCE

[75] Inventors: Jun Ma, Cincinnati; Shruti Shaw, Westchester; Daniel J. Carson; Michael J. Dorsey, both of Cincinnati, all of Ohio; Jonathan Wingfield, Northante, United Kingdom

[73] Assignee: Children's Hospital Medical Center, Cincinnati, Ohio

[21] Appl. No.: 08/812,175

[22] Filed: Mar. 6, 1997

[51] Int. Cl.$^6$ ............... C12Q 1/68; C12Q 1/02; C07H 21/04; C12N 15/81
[52] U.S. Cl. ............... 435/6; 435/4; 435/172.1; 435/254.1; 435/255.1; 435/320.1; 536/23.1; 536/24.1
[58] Field of Search ............... 435/4, 6, 29, 91.1, 435/172.1, 254.1, 255.1, 320.1; 536/23.1, 23.4

[56] References Cited

U.S. PATENT DOCUMENTS 5,534,410  7/1996  Tjian et al. ............... 435/6

OTHER PUBLICATIONS

S. Bagby, et al., "Solution Structure of the C–Terminal Core Domain of Human TFIIB: Similarity to Cyclin A and Interaction with TATA–Binding Protein", *Cell* 82:857–867 (1995).
A. Baniahmad, et al., "Interaction of human thyroid hormone receptor β with transcription factor TFIIB may mediate target gene derepression and activation by thyroid hormone", *Proc. Natl. Acad. Sci. USA* 90:8832–8836 (1993).
A. Barberis, et al., "Delineation of two functional regions of transcription factor TFIIB", *Proc. Natl. Acad. Sci. USA* 90:5628–5632 (1993).
J.D. Boeke, et al., "5–Fluoroorotic Acid as a Selective Agent in Yeast Molecular Genetics", *Methods In Enzymology* 154:164.
S. Buratowski, et al., "Five Intermediate Complexes in Transcription Initiation by RNA Polymerase II", *Cell* 56:549–561 (1989).
S. Buratowski, et al., "Functional domains of transcription factor TFIIB", *Proc. Natl. Acad. Sci. USA* 90:5633–5637 (1993).
P.M. Chevray, et al., "Protein interaction cloning in yeast: Identification of mammalian proteins that react with the leucine zipper of Jun", *Proc. Natl. Acad. Sci. USA* 89:5789–5793 (1992).
J. Colicelli, et al., "Isolation and characterization of a mammalian gene encoding a high–affinity CAMP phosphodiesterase", *Proc. Natl. Acad. Sci. USA* 86:3599–3603 (1989).
J.R. Dickinson, et al., "CEN14 sequences cause slower proliferation, reduced cell size and asporogeny in *Saccharomyces cerevisiae*", *Appl. Microbiol. Biotechnol.* 43:877–879 (1995).

S. Farrell, et al., "Gene activation by recruitment of the RNA polymerase II holoenzyme", *Genes & Development* 10:2359–2367 (1996).
G. Gill, et al., "Negative effect of the transcriptional activator GAL4", *Nature* 334:721–724 (1988).
E. Giniger, et al., "Specific DNA Binding of GAL4, A Positive Regulatory Protein of Yeast", *Cell* 40:767–774 (1985).
J.A. Goodrich, et al., "Drosophila TAF$_{II}$40 Interacts with Both a VP16 Activation Domain and the Basal Transcription Factor TFIIB", *Cell* 75:519–530 (1993).
I. Ha, et al., "Cloning of a human gene encoding the general transcription initiation factor IIB", *Nature* 352:689–695 (1991).
I. Ha, et al., "Multiple functional domains of human transcription factor IIB: distinct interactions with two general transcription factors and RNA polymerase II", *Genes & Development* 7:1021–1032 (1993).
C.J. Ingles, et al., "Reduced binding of TFIID to transcriptionally compromised mutants of VP16", *Nature* 351:588–590 (1991).
V. Joliot, et al., "Interaction with RAP74 subunit of TFIIF is required for transcriptional activation by serum response factor", *Nature* 373:632–635 (1995).
R. Knaus, et al., "Yeast SUB1 is a suppressor of TFIIB mutations and has homology to the human co–activator PC4", *The EMBO Journal* 15(8):1933–1940 (1996).
K.S. Lam, et al., "A new type of synthetic peptide library for identifying ligand–binding activity", *Nature* 354:82–84 (1991).
Y. Li, et al., "RNA Polymerase II Initiation Factor Interactions and Transcription Start Site Selection", *Science* 263:805–807 (1994).
S. Liao, et al., "A kinase–cyclin pair in the RNA polymerase II holoenzyme", *Nature* 374:193–196 (1995).
Y. Lin, et al., "Mechanism of Action of an Acidic Transcriptional Activator In Vitro", *Cell* 64:971–981 (1991).

(List continued on next page.)

*Primary Examiner*—Nancy Degen
*Attorney, Agent, or Firm*—Knobbe, Martens, Olson & Bear, LLP

[57] ABSTRACT

An extended species-specific sequence region of yeast transcription factor IIB (yTFIIB) (amino acids 144–157) is critical for cell viability and gene activation. Four residues in yTFIIB, Lys-147, Cys-149, Lys-151, and Glu-152, are critical for yeast cell growth. Intragenic suppressor experiments identified mutations that reversed, or partially reversed, the temperature sensitive phenotype of a yTFIIB derivative bearing amino acid changes at these four positions to human residues. Some of these residues (positions 115, 117 and 182) are located outside the species-specific region of yTFIIB. The identification of this species-specific region provides a unique and specific target for antifungal drugs and a screening assay therefor.

25 Claims, 10 Drawing Sheets

OTHER PUBLICATIONS

Y. Lin, et al., "Binding of general transcription factor TFIIB to an acidic activating region", *Nature* 353:569–571 (1991).

N.F. Lue, et al., "Accurate initiation at RNA polymerase II promoters in extracts from *Saccharomyces cerrevisiae*", *Proc. Natl. Acad. Sci. USA* 84:8839–8843 (1987).

J. Ma, et al., "Deletion Analysis of GAL4 Defines Two Transcriptional Activating Segments", *Cell* 48:847–853 (1987).

J. Ma, et al., "The Carboxy–Terminal 30 Amino Acids of GAL4 Are Recognized by GAL80", *Cell* 50:137–142 (1987).

E. Maldonado, et al., "News on initiation and elongation of transcription by RNA polymerase II", *Current Opinion in Cell Biology* 7:352–361 (1995).

T. Matsui, et al., "Multiple Factors Required for Accurate Initiation of Transcription by Purified RNA Polymerase II", *The Journal of Biological Chemistry* 255(24):11992–11996 (1980).

J.G. Na, et al., "The Kluyveromyces gene encoding the general transcription factor IIB: structural analysis and expression in *Saccharomyces cerevisiae*", *Nucleic Acids Research* 21(15):3413–3417 (1993).

D.B. Nikolov, et al., "Crystal structure of a TFIIB–TBP–TA-TA–element ternary complex", *Nature* 377:119–128 (1995).

J. Ozer, et al., "Molecular cloning of the small (γ) subunit of human TFIIA reveals functions critical for activated transcription", *Genes & Development* 8:2324–2335 (1994).

B. Pina, et al., "ADA3: a Gene, Identified by Resistance to GAL4–VP16, with Properties Similar to and Different from Those of ADA2", *Molecular and Cellular Biology* 13(10):5981–5989 (1993).

I. Pinto, et al., "The Yeast SUA7 Gene Encodes a Homolog of Human Transcription Factor TFIIB and Is Required for Normal Start Site Selection In Vivo", *Cell* 68:977–988 (1992).

S.G.E. Roberts, et al., "Interaction between an acidic activator and transcription factor TFIIB is required for transcriptional activation", *Nature* 363:741–744 (1993).

S.P. Shaw, et al., "Identifying a Species–Specific Region of Yeast TFIIB In Vivo", *Molecular and Cellular Biology* 16(7):3651–3657 (1996).

S.L. Wampler, et al., "Functional analysis of Drosophila transcription factor IIB", *Genes & Development* 6:1542–1552 (1992).

H. Xiao, et al., "Binding of Basal Transcription Factor TFIIH to the Acidic Activation Domains of VP16 and p53", *Molecular and Cellular Biology* 14(10):7013–7024 (1994).

R.R. Yocum, et al., "Use of lacZ Fusions to Delimit Regulatory Elements of the Inducible Divergent GAL1–GAL10 Promoter in *Saccharomyces cerevisiae*", *Molecular and Cellular Biology* 4(10):1985–1998 (1984).

W. Zhu, et al., "The N–terminal domain of TFIIB from *Pyrococcus furiosus* forms a zinc ribbon", *Nature Structural Biology* 3(2):122–124 (1996).

```
144                   157
K I V K D C A K E A Y K L C    Yeast TFIIB
R N I V D R T N N L F K Q V    Human TFIIB
R N I V D R T N N L F K Q V    Rat TFIIB
K T I V D R A N N L F K Q V    Drosophila TFIIB
R N I I D R T N N L F K Q V    Xenopus TFIIB
```

SPECIES-SPECIFIC YEAST TFIIB SEQUENCE

FIELD OF THE INVENTION

The present invention relates to a species-specific sequence within transcription factor IIB (TFIIB). More specifically, the invention relates to a vital amino acid region at the amino terminus of the first repeat of yeast TFIIB which plays an important role in determining species specificity in vivo.

BACKGROUND OF THE INVENTION

RNA polymerase II transcription in eukaryotes requires a class of proteins called general transcription factors (Maldonado et al., *Curr. Opin. Genet. Dev.,* 7:352–361, 1995). These proteins enable RNA polymerase II to recognize gene promoters and participate in the assembly of preinitiation complexes. One of these proteins, TFIIB, provides a physical link between the TATA-binding protein (TBP) and RNA polymerase II within the preinitiation complex (Barberis et al., *Proc. Natl. Acad. Sci. U.S.A.,* 90:5628–5632, 1993; Buratowski et al., *Proc. Natl. Acad. Sci. U.S.A.,* 99:5633–5637, 1993). According to a previously suggested stepwise pathway (Buratowski et al., *Cell,* 56:549–561, 1989), the first step of preinitiation complex formation is the binding of TBP to DNA. Next, TFIIB enters the complex followed by RNA polymerase II and other general transcription factors. As an integral component of the preinitiation complex, TFIIB also interacts with at least two other general transcription factors, TFIIF and a TBP-associated factor (TAF40) (Goodrich et al., *Cell,* 75:519–530, 1993; Ha et al., *Genes Dev.,* 7:1021–1032, 1993).

One of the central problems in molecular biology is to understand how transcriptional activators stimulate gene expression in eukaryotes. At the step of transcriptional initiation, activators could in principle either increase the number of preinitiation complexes by recruiting the general transcription factors or change the quality of preinitiation complexes by increasing their stability or inducing conformational changes. Many general transcription factors including TBP (Ingles et al., *Nature,* 351:588–590, 1991), TAFs (Goodrich et al., ibid.), TFIIA (Ozer et al., *Genes Dev.,* 8:2324–2335, 1994), TFIIB (Baniahmad et al., *Proc. Natl. Acad. Sci. U.S.A.,* 90:8832–8836, 1993), TFIIF (Joliot et al., *Nature,* 373:632–635, 1995) and TFIIH (Xiao et al., *Mol. Cell. Biol.,* 14:7013–7024, 1994) have been shown to interact with various transcriptional activators in vitro. In particular, a series of biochemical experiments strongly suggests that TFIIB plays an important role in transcriptional activation in vitro. First, the ability of an activator to interact with TFIIB correlates with its ability to activate transcription (Lin et al., *Nature,* 353:569–571, 1991). In addition, mutant TFIIB molecules that are defective in interacting with activators fail to support activated transcription in vitro, while basal transcription remains unaffected (Roberts et al., *Nature,* 363:741–744, 1993). Finally, transcriptional activators can stabilize the step in which TFIIB joins the preinitiation complex, a step that appears slow and/or inefficient in the absence of an activator (Lin et al., *Cell,* 64:971–981, 1991).

Despite these biochemical experiments indicating the importance of TFIIB in transcriptional activation, it is unknown if and how TFIIB participates in transcriptional activation in living cells. Although TFIIB is highly conserved among humans, rats, i Xenopus laevis, and *Drosophila melanogaster,* there is only 35% amino acid identity between yeast TFIIB (yTFIIB) and human TFIIB (hTFIIB). TFIIB molecules from eukaryotes share conserved structural motifs and are expected to form similar three-dimensional structures (Bagby et al., *Cell,* 82:857–867, 1996; Nikolov et al., *Nature,* 377:119–128, 1996). The amino-terminal domain of TFIIB contains a zinc finger motif folded into a zinc ribbon structure (Zhu et al., *Struct. Biol.,* 3:122–124, 1996). The carboxyl-terminal core domain of TFIIB is composed of two imperfect direct repeats that are similarly folded into two subdomains consisting of mainly helices (Bagby et al., ibid., Nikolov et al., ibid.). The region between these domains appears to form a flexible and extended linker region (Barbaris et al., *Proc. Natl. Acad. Sci. U.S.A.,* 90:5628–5632, 1993). As referred to herein, the amino-terminal zinc ribbon region of yTFIIB refers to amino acid residues 1–62; the linker region refers to residues 63–123; the carboxyl-terminal core domain refers to residues 124–345; and the first repeat in the carboxyl-terminal core domain refers to residues 124–226. The BH2 helix of yTFIIB refers to residues 144–161 and BH2–BH3 refers to residues 144–182.

SUMMARY OF THE INVENTION

One embodiment of the invention is a method of identifying a compound which inhibits fungal, but not human, cell growth, comprising the steps of contacting the compound with isolated human Transcription Factor IIB (hTFIIB); contacting said compound with isolated yeast Transcription Factor IIB (yTFIIB) or a fragment of yTFIIB containing lysine at position 147, cysteine at position 149, lysine at position 151 and glutamic acid at position 152; determining whether said compound binds to said yTFIIB, but not to said hTFIIB; and contacting a desired fungus with said compound which binds to said yTFIIB, but not said hTFIIB to determine whether said compound inhibits growth of said fungus. In one aspect of this preferred embodiment, the fungus is a pathogenic or nonpathogenic yeast strain. Preferably, the pathogenic yeast strain is *Candida albicans.* Advantageously, the yTFIIB fragment is, but is not limited to, the carboxy terminal core domain, the carboxy terminal core domain plus the linker region, the first repeat in the core domain, BH2, BH2–BH3 or the first repeat in the core domain plus the linker region. According to another aspect of this preferred embodiment, the determining step comprises an immunoassay. Alternatively, the determining step comprises immunoprecipitation. Preferably, the compound is labeled. The label may be radioactive, colorimetric or enzymatic. Advantageously, the yTFIIB or hTFIIB is recombinant. In addition, the yTFIIB fragment may contain glycine at position 115, asparagine at position 117 and arginine at position 182.

The present invention also provides a method of identifying a peptide fragment of yTFIIB, or a chemical compound, capable of inhibiting fungal transcription but not human transcription, comprising the steps of adding isolated yTFIIB or a fragment of yTFIIB containing lysine at position 147, cysteine at position 149, lysine at position 151 and glutamic acid at position 152 to a yeast in vitro transcription system; and adding isolated yTFIIB or a fragment of yTFIIB containing lysine at position 147, cysteine at position 149, lysine at position 151 and glutamic acid at position 152 to a human in vitro transcription system, wherein inhibition of yeast but not human transcription indicates that said compound inhibits fungal, but not human, transcription. The method may further comprise the step of contacting a desired fungus with the peptide to confirm that said peptide inhibits fungal, but not human, cell growth. Advantageously, the fungus is a pathogenic or nonpathogenic yeast strain. Preferably, the pathogenic yeast strain is *Candida albicans*. Advantageously, the yTFIIB or hTFIIB is recombinant and the yTFIIB peptides are recombinant or chemically synthesized. In another aspect of this embodiment, Lys-147, Cys-149, Lys-151 and Glu-152 are chemically modified. In addition, the yTFIIB fragment may contain glycine at position 115, asparagine at position 117 and arginine at position 182. These three positions may contain other amino acids, either native or chemically modified.

Another embodiment of the present invention is a method of identifying a peptide fragment of yTFIIB which inhibits fungal, but not human, cell growth, comprising the steps of transforming yeast cells and transfecting human cells with a vector encoding said peptide fragment of yTFIIB, said peptide fragment containing lysine at position 147, cysteine at position 149, lysine at position 151 and glutamic acid at position 152; and culturing the transformed yeast cells and transfected human cells, wherein a decrease in viability of the yeast cells, but not human cells, compared to nontransformed control cells indicates that the peptide is an inhibitor of fungal cell growth but not human cell growth. Advantageously, the fungus is a pathogenic or nonpathogenic yeast strain. Preferably, the pathogenic yeast strain is *Candida albicans*. The method may additionally comprise subjecting the vector to mutagenesis prior to the transforming step. The identified peptides are chemically synthesized or chemically modified for assays in contacting fungus as described above. The method may further comprise the step of contacting a desired fungus with the peptide to confirm that the peptide inhibits fungal, but not human, cell growth. The peptides may also be chemically modified. In another aspect of this embodiment, Lys-147, Cys-149, Lys-151 and Glu-152 are chemically modified. In addition, the yTFIIB fragment may contain glycine at position 115, asparagine at position 117 and arginine at position 182. These three positions may contain other amino acids, either native or chemically modified.

BRIEF DESCRIPTION OF THE DRAWINGS

FIG. 2 is a sequence comparison between the 14 amino acid species-specific region of yTFIIB (residues 144–157) and the corresponding sequences from other eukaryotic TFIIBs. The four critical amino acids of yTFIIB that represent the major differences from hTFIIB are underlined.

FIG. 6 illustrates the results of gain-of-function experiments in which mutant SBG (hybrid yTFIIB containing amino acids 144–166 of hTFIIB) was subjected to site directed mutagenesis within the human sequence region. Single, double and triple mutants were constructed involving residues 147, 149, 151 and 152. The changed residues are shown next to each mutant protein. The native yTFIIB sequence is shown at the bottom for comparison.

DETAILED DESCRIPTION OF THE PREFERRED EMBODIMENTS

Figure 1:
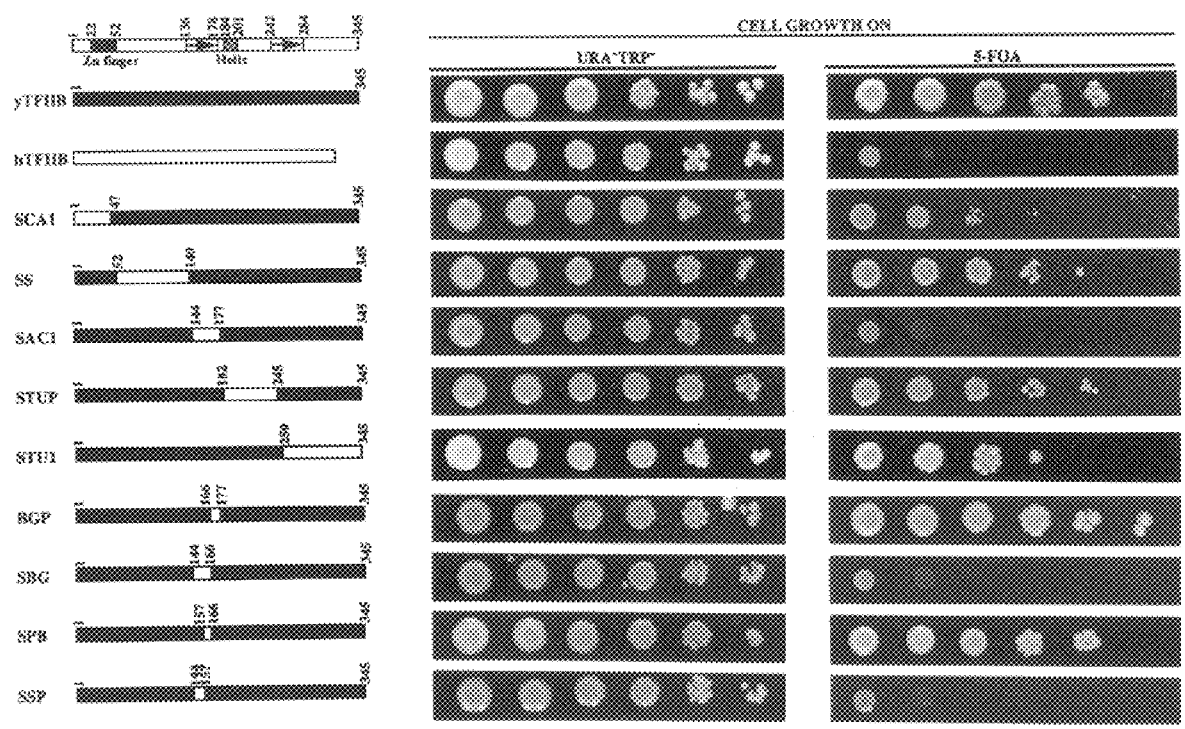
FIG. 1 shows schematic diagrams of hybrid TFIIB molecules and their abilities to function in yeast cells. Solid bars represent human sequences and open bars represent yeast sequences. Serially (10 times) diluted yeast cultures were spotted on plates containing 5-FOA, and the ability of cells to grow reflects the ability of hybrid proteins to functionally replace yTFIIB in vivo. The same serially diluted cultures were also spotted on plates lacking 5-FOA, tryptophan and uracil (URA⁻TRP⁻) to estimate the total number of cells analyzed.

The present invention includes the identification of an extended species-specific region of *Saccharomyces cerevisiae* TFIIB important for cell viability and gene activation. In in vivo plasmid shuffle experiments, hTFIIB failed to functionally replace yTFIIB in yeast cells. Various hybrid human-yeast TFIIB molecules were constructed to determine the yTFIIB region responsible for interaction with the cellular transcription apparatus. A 14 amino acid region at the amino terminus of the first repeat of yTFIIB (amino acids 144–157) was determined to play an important role in determining species specificity in vivo. Four amino acids within this region, Lys-147, Cys-149, Lys-151, and Glu-152, are vital for cell growth and in vivo activity of yTFIIB. Mutations of these residues to the corresponding four residues found in hTFIIB result in severe growth defects of cells. In addition, mutations within this region differentially affect gene expression activated by different activators in vivo. These amino acids are also critical for amphipathic helix formation unique to yeast TFIIB. Although the yTFIIB species-specific region described herein is from *S. cerevisiae*, it is reasonable to expect that this region is similar or identical to that from other species of pathogenic or nonpathogenic yeast, and in other fungal species. For example, TFIIB from the yeast species *Kluyveromyces lactis* is 67% identical (81% overall similarity) to *S. cerevisiae* TFIIB and also contains the same amino acid residues at positions 147, 149, 151 and 152 as *S. cerevisiae* TFIIB (Na et al., *Nucl. Acids Res.,* 21:3413–3417, 1993). Moreover, the amino acids in *K. lactis* corresponding to amino acids 144–157 of *S. cerevisiae* are identical. Within this region, there are only two amino acid identities between yTFIIB and hTFIIB.

As determined by construction of hybrid hTFIIB-yTFIIB genes and analysis of the encoded hybrid molecules in yeast cells, the four amino acid residues conferring yeast fungal versus human specificity are lysine 147, cysteine 149, lysine 151 and glutamic acid 152. As revealed by intragenic suppressor experiments of a mutant yTFIIB protein containing human residues at these four pivotal positions, three amino acids outside this region, namely Gly-115, Asn-117, and Arg-182, also play an important role in TFIIB activity as mutations of these amino acids restore yTFIIB activity. Because the sequence of the region of yTFIIB primarily responsible for cell viability and gene activation is specific to yeast and cannot be replaced with the corresponding human protein, this region represents an attractive target for anti-fungal drugs. Such drugs will bind to and inhibit fungal TFIIB, but will have little or no effect on hTFIIB. Such drugs can be screened for fungal inhibitory activity by a two step assay.

Prospective compounds may be screened from large libraries of synthetic or natural compounds. Peptide, nucleic acid and polysaccharide-based compounds may be synthesized by random and directed synthesis (Lam et al., *Nature,* 354:82–86, 1991). Alternatively, libraries of natural compounds in the form of bacterial, fungal, plant and animal extracts are available or readily producible. Additionally, natural and synthetically produced libraries and compounds are readily modified through conventional chemical, physical and biochemical means.

In the first step, a compound is incubated with recombinant yTFIIB or a fragment thereof containing the four species-specific amino acid residues described herein in vitro to determine whether binding occurs. One or more of these four residues may be chemically modified (i.e. methylated, carboxylated, amidated) using methods well known in the art. The recombinant production of yTFIIB and hTFIIB is well known in the art (Liao et al., *Nature,* 374:193–196, 1995; Ha et al., *Nature,* 352:689–695, 1991). yTFIIB fragments may be prepared by enzymatic digestion of full-length recombinant yTFIIB or by in vivo expression of a portion of the cDNA encoding yTFIIB. Such yTFIIB fragments containing these species-specific amino acids include, but are not limited to, the carboxy terminal core domain of yTFIIB plus the linker region, the first repeat in the core domain, and helix BH2, either alone or in the presence of BH3. These domains and helices are defined by Nikolov et al. (*Nature,* 377:119–128, 1995, incorporated be reference) for hTFIIB whose crystal structure for the carboxy-terminal core domain has been solved. The corresponding yTFIIB sequence is defined in the Background of the Invention.

Fragments of yTFIIB containing the vital amino acid residues can be incorporated into an expression vector and produced in a desired host cell. A multitude of vectors, including plasmid and viral vectors, can be used for expression in prokaryotic and eukaryotic host cells (see Pouwels et al., *Cloning Vectors: A Laboratory Manual,* Elsevier, N.Y., 1985; Rodriguez et al., eds., *Vectors. A Survey of Molecular Cloning Vectors and Their Uses,* Buttersworth, Boston, 1988, the entire contents of which are hereby incorporated by reference). Ligation of coding sequences to transcriptional regulatory sequences may be performed by known methods (Sambrook et al., *Molecular Cloning. A Laboratory Manual,* Cold Spring Harbor Laboratory Press, 1987; Ausubel et al., *Molecular Cloning, a Laboratory Manual,* 1987, both hereby incorporated by reference). Vectors may also include a promoter operably linked to the yTFIIB fragment. yTFIIB and its fragments may be tagged by epitope tags, histidine tags or both for immunodetection and protein purification, respectively.

Suitable host cells are transformed by well known methods, including, but not limited to, electroporation, calcium phosphate precipitation, viral infection and microinjection. Appropriate host cells include prokaryotes, lower eukaryotes and higher eukaryotes. Prokaryotes include both gram positive and gram negative organisms. Lower eukaryotes include yeasts and species of the genus Dictyostelium. Higher eukaryotic cells include established tissue culture cell lines from animal cells, both of non-mammalian origin (e.g. insect cells and birds) and mammalian origin (e.g., human, primate and rodent).

The compound to be tested is also incubated with recombinant hTFIIB. The compound may be labeled or unlabeled. The label can be any label well known in the art, including radiolabels, colorimetric labels, fluorescent labels or enzymatic labels.

Various assays for detecting binding of a compound to a transcription factor are described in U.S. Pat. No. 5,534,410, the entire contents of which are hereby incorporated by reference, and include protein binding assays, nucleic acid binding assays and gel shift assays. One such assay is an enzyme-linked immunosorbent assay (ELISA). Compounds of interest are bound to wells of a 96 well microtiter plate. Nonspecific binding sites are blocked with a blocking agent (i.e., nonfat dry milk) prior to addition of the yTFIIB or hTFIIB. Unbound yTFIIB or hTFIIB is removed by washing, followed by addition of an antibody against yTFIIB or hTFIIB. Enzymatically labeled (i.e. alkaline phosphatase or horseradish peroxidase-labeled) anti-IgG antibody and the appropriate enzyme substrate are added and the plate is read on a plate reader at the appropriate wavelength.

In another assay, yTFIIB or human TFIIB are bound to the wells, followed by blocking of nonspecific binding sites. A labeled compound to be tested is then added to the wells. The wells are washed to remove unbound compound. The amount of label bound to the yTFIIB wells is compared to that bound to the hTFIIB wells to determine which compounds preferentially bind to yTFIIB.

Alternatively, if the compound is labeled, the unbound labeled compound is separated from the TFIIB complex by a variety of methods well known in the art, including immunoprecipitation using an antibody against yTFIIB or the epitope tags or by gel filtration. The presence of labeled compound in the TFIIB complex indicates an interaction between the compound and TFIIB. Alternatively, a competition assay can be used in which labeled compound is bound to yTFIIB or hTFIIB in the presence of increasing concentrations of unlabeled compound. If less labeled compound is bound as the amount of unlabeled compound increases, this indicates that the compound binds to the protein. In the second step, the compounds which bind yTFIIB but do not bind to hTFIIB are then tested to determine whether they inhibit the growth of particular pathological yeast strains (i.e. *Candida albicans*) by conventional in vitro culture techniques.

In another preferred embodiment, a fragment or derivative thereof of yTFIIB capable of inhibiting yeast transcription but not human transcription is identified based on the species-specific sequence. In this method, a desired yTFIIB peptide containing the species-specific residues is added to an in vitro yeast or human transcription assay. Such transcription assays are well known in the art (Lue et al., *Proc. Natl. Acad. Sci. U.S.A.,* 84:8839–8843, 1987; Lue et al., *Science,* 246:661–664, 1989; Matsui et al., *J. Biol. Chem.,* 255:11992–11996, 1980; hereby incorporated by reference). Briefly, nuclear extracts from yeast and human cells are prepared and incubated with a DNA template in the presence or absence of a compound of interest. The in vitro transcription reaction contains nuclear extract, magnesium, template DNA and the four nucleoside triphosphates. Reactions are stopped and the resulting RNA is detected by annealing with $^{32}$P-labeled RNA probes, followed by RNase digestion and analysis of protected fragments in polyacrylamide gels. Alternatively, the RNA product is detected by primer extension (Ma et al., *Cell,* 50:137–142, 1987).

Peptides which inhibit yeast in vitro transcription but not human in vitro transcription are tested for growth inhibition of cultured pathological yeast strains. Such peptides bind to and sequester components of the transcription machinery normally involved in activation by TFIIB and other components. Thus, the peptides inhibit transcription by competing with native TFIIB for binding to proteins involved in initiation of transcription. The identified peptides can be chemically modified.

Alternatively, the assay may be performed first in yeast cells in vivo by overexpressing a yTFIIB peptide of interest containing the four vital amino acid residues described above (Gill et al., *Nature,* 334:721–724, 1989; Ma et al., *Cell,* 50:137–142, 1987; Farrel, *Genes Dev.,* 10:2359, 1996; hereby incorporated by reference). The identified peptide, or its modified form, is assayed for anti-fungal activity as described above.

A yeast plasmid shuffle system (Boeke et al., *Methods. Enzymol,* 154:164–175, 1987) was used to determine whether hTFIIB could functionally replace yTFIIB in vivo as described below.

EXAMPLE 1
Replacement of yTFIIB in vivo

Briefly, the entire coding sequence of the endogenous yTFIIB gene in *S. cerevisiae* S150B (a leu2-2 his3 trp1-289 ura3-52) (Wingfield et al., *Appl. Microbiol. Biotechnol.,* 39:211–215, 1993) was deleted by replacement with the LEU2 gene, while cell viability was maintained by a URA3 plasmid expressing the wild-type yTFIIB (pDW5462) (Pinto et al., *Cell,* 68:977–988, 1992). TRP1 plasmids expressing various hybrid TFIIB molecules were transformed into yeast strains and TRP1$^+$ URA3$^+$ transformants were grown in liquid media lacking tryptophan and uracil. Serially diluted (10-fold) liquid cultures were spotted on either minimal plates lacking tryptophan and uracil or plates containing 5-fluoroorotic acid (5-FOA) and incubated at 30° C.

In this method, pDW5462 which carries a yeast URA3 gene, was eliminated from yeast cells with 5-FOA, a chemical toxic to cells expressing the URA3 gene. Thus, the ability of yeast cells to grow on 5-FOA plates reflects the in vivo activity of TFIIB expressed from the second (TRP1) plasmid. While yeast cells expressing yTFIIB grew well on 5-FOA plates as expected, those expressing hTFIIB completely failed to survive the 5-FOA selection (FIG. 1). These results suggest that yTFIIB and hTFIIB are specific to their respective species in vivo.

To determine which putative structural motif or other region of yTFIIB determined the species specificity, hybrid genes were generated encoding yTFIIB derivatives with various motifs and/or regions replaced by their corresponding human sequences.

EXAMPLE 2
Generation and analysis of hybrid yTFIIB-hTFIIB molecules

Figure 4:
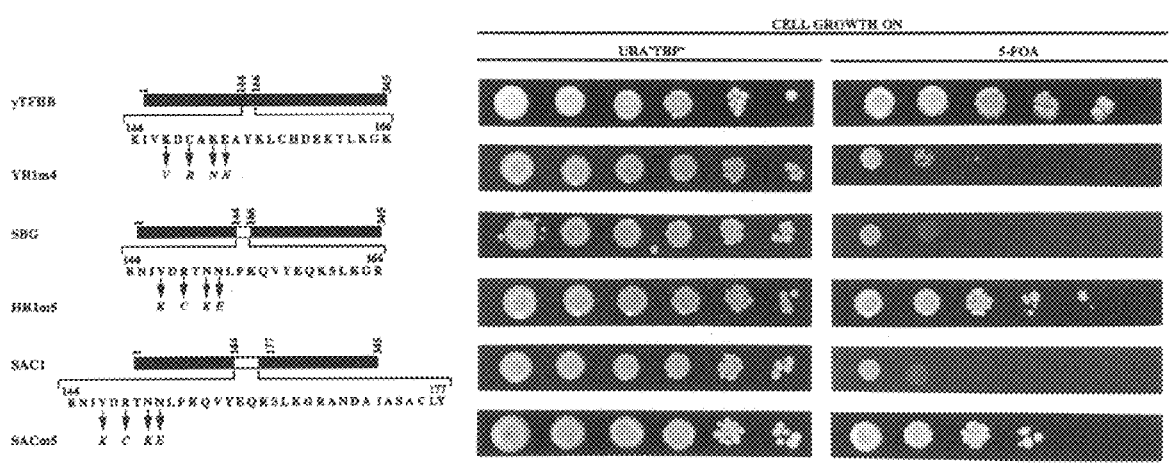
FIG. 4 illustrates the results of loss-of-function and gain-of-function analyses. Mutant yTFIIB genes were constructed by site-directed mutagenesis and assayed as described for FIG. 1. Amino acids 147, 149, 151 and 152 were mutated from the yeast to human residues (loss-of-function) (YR1m4) or from human to yeast residues (gain-of-function) (HR1m5, SACm5).
Figure 8:
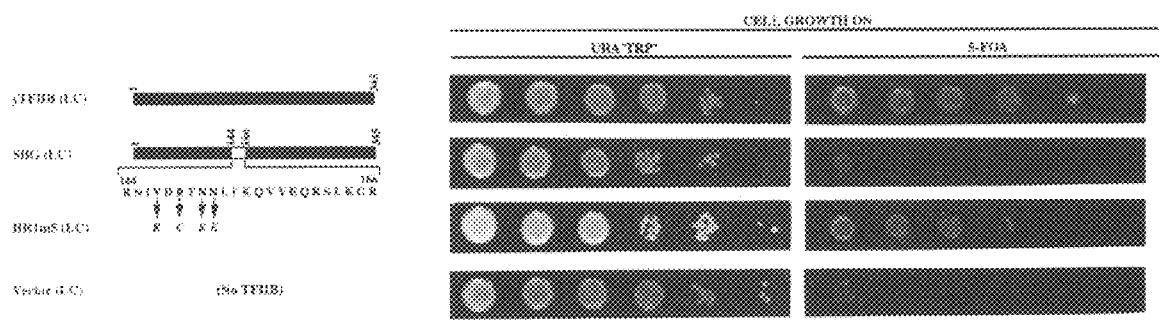
FIG. 8 shows TFIIB derivatives at physiological levels. The indicated TFIIB derivatives were expressed from the yTFIIB promoter on a low-copy-number (LC) ARS-CEN vector. Their abilities to complement the endogenous yTFIIB protein were determined in an assay similar to those for FIGS. 1 and 4.

The following regions were tested individually: (i) the amino terminus, including the zinc finger motif (SCA1); (ii) the region between the zinc finger motif and the first repeat (SS); (iii) the first repeat (SAC1); (iv) the region between the two repeats, which includes the putative helix (STUP); and (v) the entire carboxy terminus, which includes the second repeat (STU1) (FIG. 1). These structural regions are those of Pinto et al. (*Cell,* 68:977–988, 1992) and are slightly different from the structural information according to the hTFIIB core domain.

pMA1210A, a TRP1 2 µm plasmid expressing the wild type yTFIIB from the ADH1 promoter, was constructed from pADNS (Colicelli et al., *Proc. Natl. Acad. Sci. U.S.A.,* 86:3599–3603, 1989) and pDW5462. All hybrid genes were first constructed by polymerase chain reaction (PCR), then transferred to the backbone of pMA1210A. The gene encoding SSP, which was generated from the inactive derivative SAC1, was verified by DNA sequencing. A site-directed mutagenesis procedure based on PCR was used to generate the genes for loss-of-function and gain-of-function experiments whose results are shown in FIG. 4. For experiments whose results are shown in FIG. 8, the yTFIIB promoter sequence was first inserted into pPC86, an ARS-CEN plasmid (Chevray et al., *Proc. Natl. Acad. Sci. U.S.A.,* 89:5789–5793, 1992), to create the vector BLC0. The yTFIIB genes were then transferred to this vector and analyzed in the plasmid shuffle system.

While yeast cells bearing SAC1 completely failed to grow on 5-FOA plates, those bearing each of the other derivatives all survived this selection to various extents (FIG. 1). This demonstrates that each of the individual regions of yTFIIB, with the exception of the first repeat, can be functionally replaced by its corresponding human sequence.

To further define the region responsible for determining species specificity of yTFIIB, shorter segments in the first repeat of yTFIIB were exchanged with the corresponding hTFIIB regions. First, hybrid genes were constructed encoding TFIIB derivatives with either the amino-terminal (SBG) or the carboxy-terminal (BGP) half of the first repeat of yTFIIB replaced by the corresponding human sequence (FIG. 1), while cells bearing BGP grew well on 5-FOA plates, cells bearing SBG did not grow at all (FIG. 1), demonstrating that the amino-terminal half of the first repeat of yTFIIB is non-exchangeable. Additional hybrid genes were generated by further dividing this non-exchangeable region into the amino-terminal (SSP) and carboxy-terminal (SPB) halves (FIG. 1). While cells containing SPB grew well on 5-FOA plates, cells containing SSP virtually failed to grow on 5-FOA plates (FIG. 1), suggesting that the amino-terminal quarter of the first repeat of yTFIIB is non-exchangeable. A small number of cells bearing SSP eventually grew on 5-FOA plates, but the number of surviving cells was 3 to 4 orders of magnitude lower than that for cells bearing SPB or wild type yTFIIB (FIG. 1). In addition, the surviving cells bearing SSP grew extremely slowly on both synthetic and rich medium plates and exhibited a temperature-sensitive phenotype.

Figure 3:
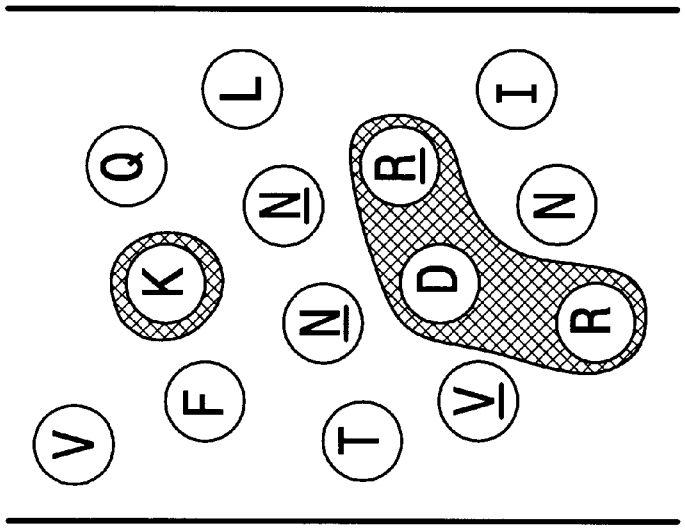
FIG. 3 is a schematic diagram of amphipathic helices formed from the 14 amino acid species-specific region of yTFIIB and the corresponding human sequence. Shaded areas indicate charged surfaces, and the underlined four residues represent the major differences between yTFIIB and hTFIIB. The human helix represents part of helix BH2 in the crystal structure of hTFIIB.
Figure 3:
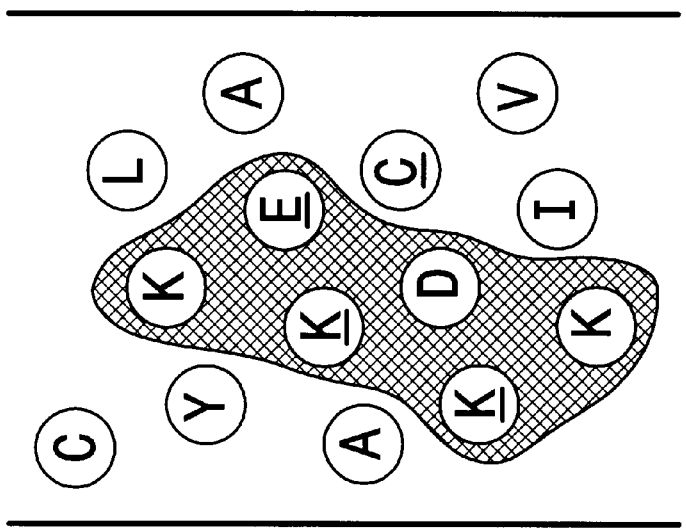

The non-exchangeable region in the first repeat of yTFIIB contains 14 amino acids (residues 144 to 157). Although this region is highly conserved among TFIIBs from humans, rats, *X. laevis,* and *D. melanogaster,* consistent with the previous demonstration that hTFIIB and Drosophila TFIIB are functionally interchangeable in vitro (Wampler et al., *Genes Dev.,* 6:1542–1552, 1992), only two amino acids are identical between yTFIIB and hTFIIB in this region (FIG. 2). According to the recently published structure of hTFIIB (Bagby et al., *Cell,* 82:857–867, 1995; Nikolov et al., *Nature,* 377:119–128, 1995), the region corresponding to the species-specific region of yTFIIB is folded into part of a solvent-exposed helix (designated BH2). All known eukaryotic TFIIBs may form similar structures. Accordingly, the species-specific region in yTFIIB could be similarly folded into a solvent-exposed helix. The yTFIIB helix would be amphipathic, with charged residues (net charge, +2) on one side and hydrophobic residues on the other (FIG. 3). The corresponding human helix has fewer charged residues, though with the same net charge (FIG. 3). In addition, the relative positions of the charged surfaces of the respective helices are slightly different (FIG. 3). These potential structural differences are mainly contributed by four amino acid residues at positions 147, 149, 151 and 152 that differ between yTFIIB and hTFIIB (underlined in FIGS. 2 and 3).

To determine whether the amphipathic helix at the amino terminus of the first repeat of yTFIIB is important for the protein's activity in vivo, two different analyses were performed by changing the four critical amino acids as described below.

EXAMPLE 3
Gain-of-function and loss-of-function analyses

In a loss-of-function assay, a mutant yTFIIB gene was generated encoding an otherwise wild type yTFIIB with only these four residues changed to the corresponding human residues (YR1m4) (FIG. 4). The ability of yeast cells bearing this derivative to grow on 5-FOA plates was significantly impaired (FIG. 4). The number of cells surviving 5-FOA selection was three orders of magnitude lower than that for cells bearing the wild type yTFIIB (FIG. 4). In addition, the surviving cells grew noticeably slower and exhibited a temperature-sensitive phenotype. These results suggest that these four amino acids of yTFIIB are essential for its activity in vivo.

In another detailed loss-of-function experiment (FIG. 5), the amino acids at the four critical positions of yTFIIB were changed, either individually or in triplets, to the corresponding human residues. Each mutant derivative is assigned a number following the letter L (for loss-of-function). The ability of these derivatives to support cell growth is summarized in FIG. 5. yTFIIB derivatives bearing individual amino acid changes (L1–L4) did not show any detectable decrease in the protein's ability to support cell growth. In addition, none of the derivatives bearing triple changes (L5–L8) showed any dramatic decrease in the protein's ability to support cell growth. The results obtained with the triple mutation derivatives of yTFIIB indicated that double mutation derivatives would most likely have little effect on in vivo protein function. Therefore, all possible double mutation derivatives were not examined. Consistent with the results described in FIG. 4, derivative L9 (YR1m4 in FIG. 4) is functionally impaired.

These results suggest that changes in all four positions of yTFIIB are required to generate a severe loss-of-function phenotype.

In a gain-of-function assay, the corresponding four human residues were converted to yeast residues in two inactive hybrid derivatives (SBG and SAC1 to HR1m5 and SACm5, respectively) (FIG. 4). Yeast cells bearing these modified hybrid derivatives gained the ability to grow on 5-FOA plates (FIG. 4), indicating that these four amino acids from yTFIIB are sufficient to confer biological function to these inactive yeast-human hybrid derivatives. Taken together, the results demonstrate that the four amino acids (Lys-147, Cys-149, Lys-151 and Glu-152) which are important for the amphipathic helix BH2 of yTFIIB, provide essential species-specific functions in vivo. Consistent with our results, a temperature sensitive mutant of yTFIIB isolated by Knaus et al. (*EMBO J,* 15:1933–1940, 1996) had a change of cysteine to arginine at amino acid 149.

Figure 6:
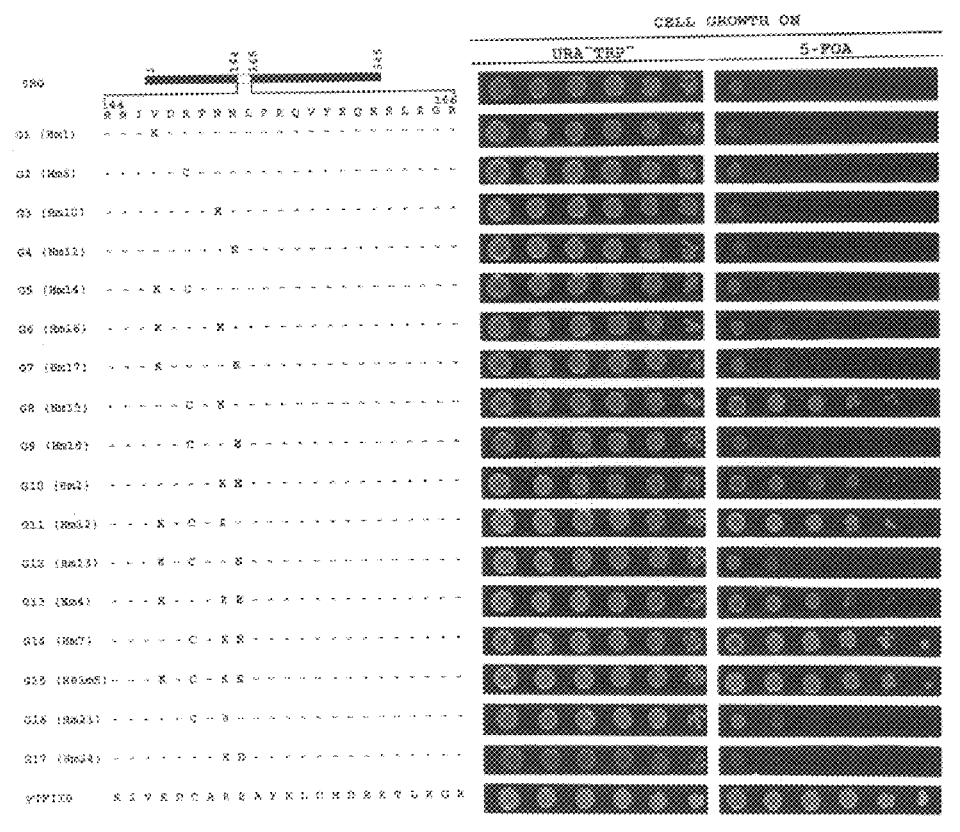

In another detailed gain-of-function experiment (FIG. 6), the four critical amino acid positions (147, 149, 151 and 152) were analyzed. By site-directed mutagenesis, we generated SBG derivatives bearing individual, double or triple amino acid changes from human back to yeast residues. Each mutant derivative in FIG. 6 is assigned a number followed by the letter G (for gain-of-function). None of the SBG derivatives with individual amino acid changes from human back to yeast residues (G1–G4) was able to support cell growth. Among all the derivatives with double changes (G5–G10), only G8 and G10 supported cell growth significantly. Both of these derivatives include a change at position 151 from asparagine to the native yeast residue lysine, indicating the importance of this position in yTFIIB function. All derivatives bearing triple changes (G11–G14), except G12 which has a human residue at position 151, supported cell growth efficiently. Derivative G14, similar to the derivative bearing all four amino acid changes (G15, called HR1m5 in FIG. 4), supported cell growth as efficiently as wild type yTFIIB. These results are consistent with the idea that, among the four positions systematically tested, position 151 is the most critical for the function of yTFIIB in vitro, followed by positions 149 and 152, and finally position 147.

Figure 5:
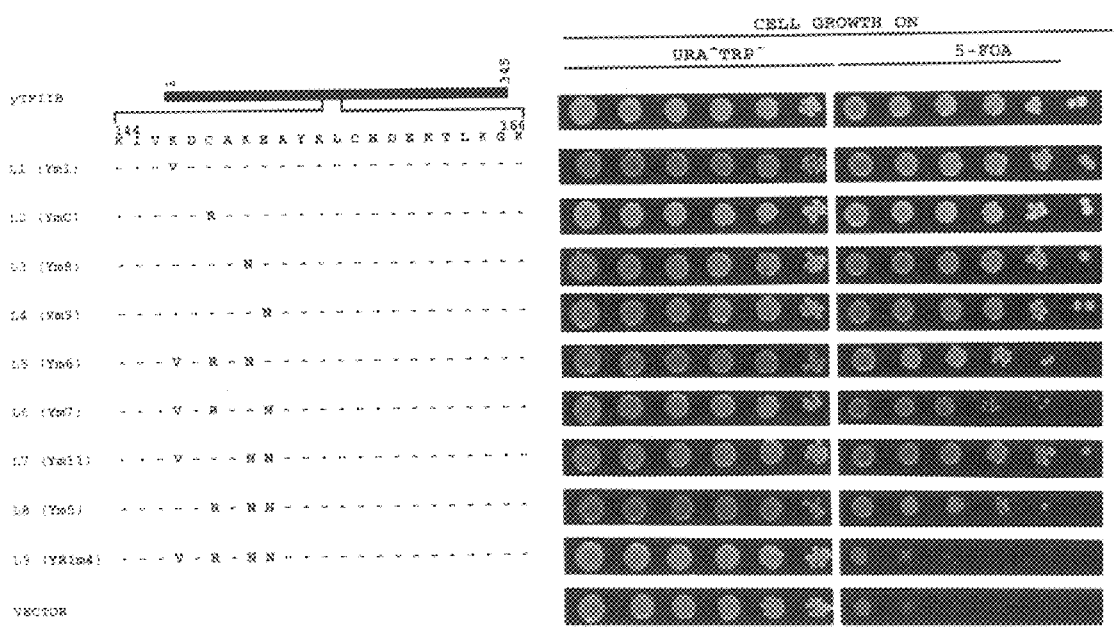
FIG. 5 illustrates the results of loss-of-function experiments in which single or triple mutations were performed in the yTFIIB sequence at residues 144, 147, 151 and 152.

These gain-of-function and loss-of-function experiments were conducted in two different contexts and their results were not expected to be simple mirror images of each other. The results described herein clearly demonstrate that more amino acid changes are required to inactivate wild type TFIIB than to re-gain the function of the inactive hybrid yTFIIB derivative SBG (FIGS. 5 and 6).

Two amino acids at the three most critical positions in the species-specific region of yTFIIB, Lys-151 and Glu-152, are charged. To determine whether their respective charges or amino acid side chains are important for the function of yTFIIB in vivo, two additional derivatives, G16 and G17, were generated (FIG. 6). In these two double-mutation derivatives, amino acids at positions 151 and 152 are changed to arginine and aspartic acid, respectively, rather than to the native yeast residues lysine and glutamic acid (G8 and G10), thus introducing identical charges but different side chains at these positions. The results obtained from G16 and G17, in comparison with those from G8 and G10, respectively, strongly suggest that the amino acid side chains at positions 151 and 152, rather than their charges alone, are important for the function of yTFIIB in vivo. These results are consistent with the idea that the species-specific region of yTFIIB is involved in protein-protein interactions.

Figure 7:
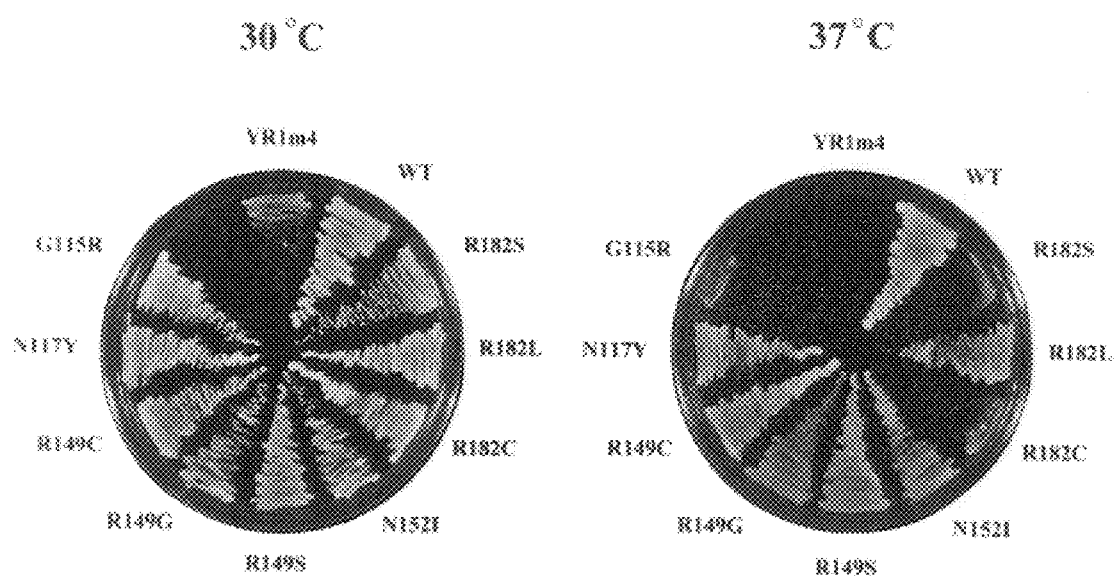
FIG. 7 shows wild type yTFIIB, YR1m4, or various intragenic suppressor mutants of YR1m4 grown on YEPD plates at 30° C. and 37° C.

Yeast cells bearing YR1m4 (FIG. 5) but lacking wild type yTFIIB completely failed to grow at 37° C. (FIG. 7). Spontaneous intragenic suppressor mutations of this mutant yTFIIB gene were isolated to determine whether the mutation could be reversed or partially reversed as described below.

EXAMPLE 4
Analysis of intragenic suppressor mutations

Spontaneous mutations of the YR1m4 mutant yTFIIB gene were isolated that enabled yeast cells to grow at 37° C. to various extents (FIG. 7). Plasmids carrying the mutant yTFIIB genes were purified from these yeast cells and transformed into a fresh yeast strain to confirm that the suppression phenotype was linked to the plasmids. A yeast strain expressing YR1m4 from a TRP1 plasmid, but lacking the chromosomal copy of yTFIIB, was generated by 5-FOA selection. To completely eliminate the wild type yTFIIB gene carried on the URA3 plasmid, two rounds of 5-FOA selection were preformed. A total of 26 independent 10 ml YEPD liquid cultures (approximately $3.1 \times 10^9$ cells) were grown at 30° C. for one day, then plated on separate YEPD plates and incubated at 37° C. until colonies appeared. Separate liquid cultures of small volumes were used to minimize the possibility of isolating non-independent, clonal suppressor mutants.

Most plates had few or no colonies. A maximum of three colonies were picked from each plate. Yeast colonies were grown in YEPD liquid cultures at 30° C. and plasmid DNA was isolated and amplified in *E. coli*. Plasmids were retransformed into a fresh plasmid shuffle yeast strain to confirm that the suppression phenotype was linked to the plasmids. For the experiments summarized in Table 1, a total of 38 yTFIIB suppressor genes were isolated and sequenced to identify the mutations, 36 of which are listed in the table.

In most cases, with the exception of six plates, multiple suppressor mutants isolated from the same YEPD plate revealed point mutations leading to different amino acid changes. Each suppressor gene contained a single base pair change. Table 1 summarizes the amino acid changes, number of times each change was identified and the ability of each intragenic suppressor to support cell growth at both 30° C. and 37° C. The suppressor mutants are named according to the amino acid changes, although it should be noted that the starting protein, YR1m4, is itself a mutant bearing four changes at positions 147, 149, 151, and 152 from yeast to human amino acids. The ability of each intragenic suppressor to support cell growth at both 30° C. and 37° C. is shown in FIG. 7 and summarized in Table 1. YR1m4 is a stable protein in yeast cells and the suppressor mutants most likely do not simply change the stability of the proteins. Many mutations were isolated independently more than once, suggesting that this screening assay resulted in the recovery of most of the possible suppressor mutations.

TABLE 1

|  |  | Cell growth at | |
| --- | --- | --- | --- |
| Mutation | times isolated | 30° C. | 37° C. |
| R149C | 13 | ++++ | ++++ |
| R149S | 5 | ++++ | ++++ |
| R149G | 4 | +++ | +++ |
| N152I | 1 | ++++ | +++ |
| R182L | 4 | ++++ | +++ |
| R182S | 3 | ++++ | + |
| R182C | 3 | +++ | + |
| G115R | 1 | +++ | +/− |
| N117Y | 2 | ++++ | +++ |
| YR1m4 | N/A | + | − |
| yTFIIB | N/A | +++++ | +++++ |

The intragenic suppressor experiment revealed amino acid changes at five positions, two of which had been originally mutated in YR1m4. First, Arg-149 was changed to, with a decreasing ability to support cell growth, cysteine, serine and glycine. Second, Asn-152 was changed to isoleucine. It should be noted that a reversion of Asn-152 to the native yeast residue glutamic acid requires more than a single base pair change and, therefore, was not isolated in this screening. Mutants changing either Asn-151 or Val-147 back to the native yeast residue lysine were not isolated because such mutants generated by site-directed mutagenesis (L6 and L8, respectively, in FIG. 5) remained temperature sensitive.

The remaining three positions of amino acid changes revealed by the intragenic suppressor experiment are located outside the four residues originally mutated in YR1m4. Arg-182 was changed to, with a decreasing ability to support cell growth, leucine, serine and cysteine. In addition, Gly-115 and Asn-117 were changed to arginine and tyrosine, respectively (the hTFIIB residues corresponding to Gly-115, Asn-117 and Arg-182 of yTFIIB are asparagine, arginine and glutamine, respectively). The results shown in FIG. 7 and Table 1 imply that several suppressor mutations (e.g. G115R, R182S and R182C) resulted in a much improved cell growth phenotype at 30° C. than at 37° C. The ability of these mutant proteins to support cell growth at 30° C. and 37° C. may reflect slightly different aspects of their functional properties in vivo.

In the experiments whose results are shown in FIGS. 1, 4, 5, and 6, all TFIIB derivatives were expressed from the strong ADH1 promoter on multicopy plasmids to ensure high protein levels in yeast. To verify that the observed phenotypes were due to functional differences rather than protein levels, immunoblotting experiments of yeast protein extracts was performed as described below.

EXAMPLE 5
Immunoblotting of yeast protein extracts

An oligonucleotide encoding a hemagglutinin tag was fused to the first codon of the TFIIB genes. Yeast cells transformed with these modified plasmids were grown in 50 ml synthetic media lacking uracil and tryptophan with 2% glucose. Proteins extracted from about $10^7$ cells were separated by SDS-PAGE, transferred to nitrocellulose, blotted with an anti-hemagglutinin monoclonal antibody (HA.11, Berkeley Antibody Co., 1:300 final dilution), and visualized by enhanced chemiluminescence (Amersham). A monoclonal antibody (C4, 6 μg/ml final concentration) against the conserved region of actin was used to determine the actin level as an internal control.

Most TFIIB proteins were present in yeast cells at comparable levels. These levels were all higher than yTFIIB expressed from its own promoter on a single-copy plasmid. In this immunoblotting assay, STUP was present at a lower level than the others and a faster-moving band may represent a proteolytic product. STUP is a functional TFIIB derivative in yeast cells and none of the inactive derivatives accumulated at lower levels. These results strongly suggest that the observed phenotypes of the TFIIB proteins were due to their functional differences rather than to protein levels.

Several key TFIIB proteins expressed at physiological levels, rather than overexpressed, were also analyzed. In the experiments whose results are described in FIG. 8, all proteins were expressed from the yTFIIB promoter on ARS-CEN plasmids. As expected, wild type yTFIIB expressed from the plasmid was able to complement the endogenous yTFIIB gene. A hybrid TFIIB derivative (SBG) with yeast residues 144 to 166 replaced by the corresponding human sequence was completely inactive in yeast cells. Conversion of the four human amino acid residues to yeast residues (HR1m5) restored its in vivo function. These results demonstrate that the TFIIB derivatives expressed at physiological levels behave identically to their respective overexpressed proteins.

EXAMPLE 6
Determination of transcription start sites

TFIIB is involved in determining transcription start sites (Li et al., Science, 263:805–807, 1994; Pinto et al., ibid.). Transcription starts about 40 to 120 base pairs (bp) downstream of the TATA box in S. cerevisiae and about 30 bp downstream of the TATA box in humans (Li et al., ibid.). Yeast cells bearing either the wild type or mutant YR1m4 yTFIIB were grown in 20 ml of YPD medium. Total RNA was isolated and primer extension analysis was performed as described previously (Ma et al., Cell, 48:847–853, 1987). Transcription start sites were determined in yeast cells bearing various yTFIIB derivatives either in the presence of wild type yTFIIB when the derivatives were nonfunctional or in the absence of yTFIIB when they were sufficiently functional to support cell viability.

No start sites indicative of the human transcription system were detected. These results are consistent with those of previous studies demonstrating that the difference between S. cerevisiae and other eukaryotes in start site selection is mediated by RNA polymerase II and TFIIB together (Li et al., ibid.). In these experiments only minor alterations of transcription start sites were detected. For example, the relative intensities of the two major start sites of the ADH1 gene were slightly altered in cells bearing a mutant yTFIIB. In addition, a weak start site between the two major start sites was enhanced, and several new start sites, though very weak, were detected in cells bearing the mutant yTFIIB. It should be noted that despite these minor alterations, these experiments clearly demonstrate the lack of a gross shift of transcription start sites from yeast to human positions. Therefore, it is unlikely that the defects of these yTFIIB mutants in fully supporting cell growth are solely caused by such a gross shift of transcription start sites.

Previous studies suggest that TFIIB plays an important role in gene regulation. Thus, one potential function of the species-specific region of yTFIIB may be mediation of transcriptional activation in vivo. The following example addresses whether mutations in this region of yTFIIB affects the ability of activators to activate transcription in yeast cells.

EXAMPLE 7
In vivo gene activation by mutant yTFIIB

Although the in vivo activity of the derivative YR1m4 was significantly impaired (FIG. 4), a small number of cells bearing this derivative survived 5-FOA selection. After 5-FOA selection, yeast cells bearing either YR1m4 or wild type yTFIIB were transformed with URA3 plasmids carrying CYC1-lacZ reporter genes under control of HAP1, HAP2/3/4/5, GCN4, GAL4 or no activators (Giniger et al., Cell, 40:767–774, 1985; Pina et al., Mol. Cell. Biol, 13:5981–5989, 1993). These reporter genes contain identical promoter elements from the CYC1 gene, including the TATA boxes and transcription initiation sites, and only the activator binding sites are different.

Figure 9:
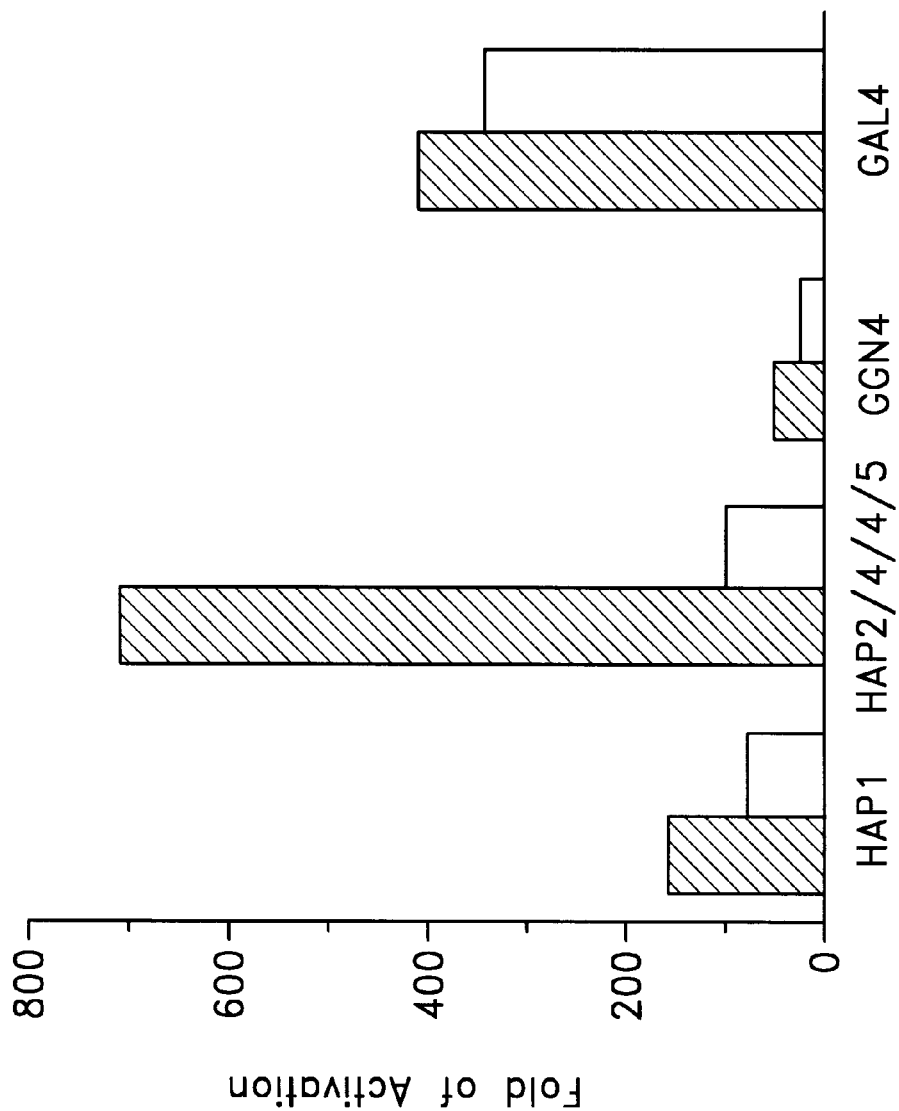
FIG. 9 illustrates the effect of mutations in the species-specific region of yTFIIB on gene activation in vivo. CYC-lacZ reporter genes under the control of various activators were transformed into yeast cells containing either the wild type (solid bars) or mutant YR1m4 (open bars) yTFIIB. β-galactosidase activities obtained from the reporter gene without any activator binding sites were used as nonactivated levels of transcription. Fold activation was calculated by dividing the β-galactosidase activities by the nonactivated levels of transcription in each strain. The binding sites for the activators were UAS1, UAS2UP1, a HIS4 oligonucleotide and a synthetic GAL4 binding site, respectively.

Yeast transformants were grown in glucose (2%) liquid culture lacking uracil until saturation, diluted in galactose (2%) liquid medium, incubated until the optical density at 600 nm reached 1 to 1.5 and assayed for β-galactosidase activity as previously described (Ma et al., ibid.; Yocum et al., Mol. Cell. Biol., 4:1985–1998, 1984). The results (FIG. 9) show that the mutations in the species-specific region of yTFIIB can differentially affect the expression of genes activated by different activators in vivo. In these experiments, the nonactivated levels of transcription in the absence of any known activators were similar in cells bearing either the wild-type or mutant yTFIIB (1.4 and 0.8 U of μ-galactosidase, respectively), suggesting that the mutant yTFIIB can properly interact with other general transcription factors in vivo. Extents of activation by GAL4, as measured by fold activation over nonactivated levels of transcription, were very similar in cells bearing either the wild type or mutant yTFIIB (411- and 344-fold, respectively; FIG. 9), further demonstrating that this mutant yTFIIB is not simply an inactive protein. Activation of GCN4 and HAP1 was modestly affected in cells bearing the mutant yTFIIB (FIG. 9). Consistently, it was found that yeast cells bearing this mutant yTFIIB remained Gal$^+$ and His$^+$ (data not shown), two phenotypes requiring the expression of genes activated by GAL4 and GCN4, respectively. In contrast, activation by HAP2/3/4/5 was sharply decreased in cells bearing the mutant yTFIIB (from 706- to 98-fold activation). Because the mutations in the species-specific region of yTFIIB do not affect gene expression indiscriminately, this mutant yTFIIB (and possible other inactive mutants) may fail to support cell growth because of decreased (or abolished) expression of only a subset of, rather than all, essential yeast genes.

Figure 10:
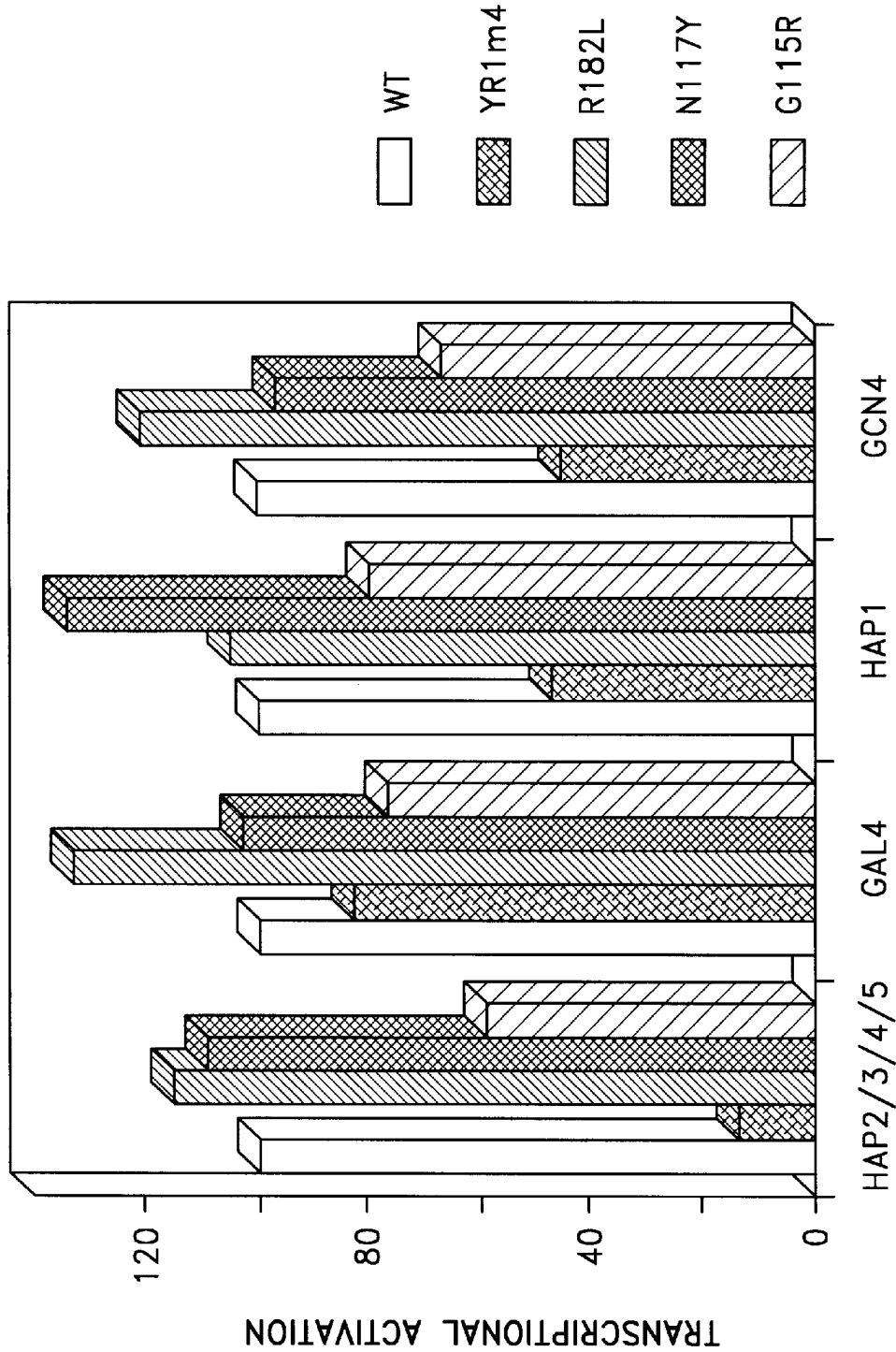
FIG. 10 shows the results of gene activation experiments in which CYC-lacZ reporter genes under the control of various activators or no activators were assayed in yeast cells containing either wild type yTFIIB, YR1m4, or the intragenic suppressor mutants R182L, N117Y and G115R. Transcriptional activation by each activator, calculated by dividing the activated levels of expression by the non-activated levels of transcription, was shown as percentage of activation obtained in the wild type yTFIIB strain.

Three of the intragenic suppressor mutants, R182L, N117Y, and G115R (FIG. 10) were analyzed to determine whether the defect in mediating gene activation was reversed. As shown in FIG. 10, both R182L and N117Y completely restored the expression of the target gene activated by HAP2/3/4/5. The activation by other activators, HAP1 and GCN4, was also increased to wild type levels. Gene activation was partially restored in yeast cells bearing G115R (FIG. 10), an intragenic suppressor mutant that only partially reversed the temperature sensitive phenotype. These results strongly suggest that the defects of L9 (YR1m4) in mediating gene activation and in fully supporting cell growth are associated.

The results described hereinabove suggest that an extended surface of yTFIIB is important for its function in vivo. Both gain-of-function and loss-of-function experiments suggest that four amino acids positions in the yeast-specific region of yTFIIB (Lys-147, Cys-149, Lys-151 and Glu-152), in particular positions 151, 149 and 152, are important for the protein's ability to support cell growth. According to the hTFIIB structure (Bagby et al., Cell, 82:857–867, 1995; Nikolov, Nature, 377:119– 128, 1995), these amino acid positions are located on the solvent exposed side of the second helix (BH2) in the first repeat of the carboxy terminal core domain. One of the amino acid positions revealed in the intragenic suppressor analysis, Lys-182, is located at the end of the third helix (BH3). The hTFIIB structure suggests that this solvent exposed residue of yTFIIB and the four amino acids in the yeast-specific region form an extended surface.

No structural information is currently available for the region surrounding Gly-115 and Asn-117 of yTFIIB. The hTFIIB amino acid positions corresponding to Gly-115 and Asn-117 of yTFIIB are only 8 and 6 residues away, respectively, from the amino terminus of the hTFIIB core domain. Previous studies suggest that this region is a flexible and extended linker between the amino terminal zinc finger domain and the carboxy terminal core domain (Barberis et al., Proc. Natl. Acad. Sci. U.S.A., 90:5628–5632, 1993). Based on their projected proximity to each other, positions 115 and 117, together with BH2 and position 182 at the end of BH3, are likely to form a further extended surface. It is believed that all amino acid positions discussed herein form an extended functional surface. Mutations at these positions, unlike those involving residues located in the interior of the protein, are less likely to induce a gross conformational alteration. In addition, none of these amino acids of yTFIIB is located near the corresponding hTFIIB sequences involved in an intramolecular interaction and a conformational change induced by VP16 (Roberts et al., *Nature*, 371:717–720, 1994).

The experiments shown in FIG. 6 (G16 and G17) demonstrate that amino acid side chains at positions 151 and 152, rather than their charges alone, are important for the function of yTFIIB in vivo, further supporting the idea that the species-specific surface is involved in protein-protein interaction. In some of the intragenic suppressor mutants, positions 149 and 152 were changed to residues not native to yTFIIB (Table 1), indicating that these positions can tolerate a subset of, but not any, amino acid residues. Amino acid positions revealed in this study may not represent the entire functional surface of yTFIIB because other solvent exposed residues important for protein-protein interactions may be conserved and/or invariable.

What is claimed is:

1. A method of identifying a compound which inhibits fungal, but not human, cell growth, comprising the steps of:
    contacting said compound with isolated human Transcription Factor IIB (hTFIIB);
    contacting said compound with isolated yeast Transcription Factor IIB (yTFIIB) or a fragment of yTFIIB containing lysine at position 147, cysteine at position 149, lysine at position 151 and glutamic acid at position 152;
    determining whether said compound binds to said yTFIIB, but not to said hTFIIB; and
    contacting a desired fungus with said compound which binds to said yTFIIB, but not said hTFIIB to determine whether said compound inhibits growth of said fungus.

2. The method of claim 1, wherein said fungus is a pathogenic or nonpathogenic yeast strain.

3. The method of claim 2, wherein said pathogenic yeast strain is *Candida albicans*.

4. The method of claim 1, wherein said yTFIIB fragment is selected from the group consisting of the carboxy terminal core domain, the carboxy terminal core domain plus the linker region, the first repeat in the core domain, BH2, BH2-BH3 and the first repeat in the core domain plus the linker region.

5. The method of claim 1, wherein the determining step comprises an immunoassay.

6. The method of claim 1, wherein the determining step comprises immunoprecipitation.

7. The method of claim 1, wherein said compound has a label.

8. The method of claim 1, wherein said label is radioactive, calorimetric or enzymatic.

9. The method of claim 1, wherein said yTFIIB or said hTFIIB is recombinant or tagged with epitope and/or histidine tags.

10. The method of claim 1, wherein said Lys-147, Cys-149, Lys-151 and Glu-152 are chemically modified.

11. The method of claim 1, wherein said yTFIIB fragment contains glycine at position 115, asparagine at position 117 and arginine at position 182.

12. A method of identifying a peptide fragment of yTFIIB capable of inhibiting fungal transcription but not human transcription, comprising the steps of:
    adding yTFIIB or a fragment of yTFIIB containing lysine at position 147, cysteine at position 149, lysine at position 151 and glutamic acid at position 152 to a yeast in vitro transcription system; and
    adding yTFIIB or a fragment of yTFIIB containing lysine at position 147, cysteine at position 149, lysine at position 151 and glutamic acid at position 152 to a human in vitro transcription system,
wherein inhibition of yeast but not human transcription indicates that said compound inhibits fungal, but not human, transcription.

13. The method of claim 12, further comprising the step of contacting a desired fungus with said peptide to confirm that said peptide inhibits fungal, but not human, cell growth.

14. The method of claim 13, wherein said fungus is a pathogenic or nonpathogenic yeast strain.

15. The method of claim 14, wherein said pathogenic yeast strain is *Candida albicans*.

16. The method of claim 12, wherein said yTFIIB or fragment thereof is recombinant or chemically synthesized.

17. The method of claim 12, wherein said Lys-147, Cys-149, Lys-151 and Glu-152 are chemically modified.

18. The method of claim 12, wherein said yTFIIB fragment contains glycine at position 115, asparagine at position 117 and arginine at position 182.

19. A method of identifying a peptide fragment of yTFIIB which inhibits fungal, but not human, cell growth, comprising the steps of:
    transforming yeast cells with a vector encoding said peptide fragment of yTFIIB, said peptide fragment containing lysine at position 147, cysteine at position 149, lysine at position 151 and glutamic acid at position 152;
    transforming human cells with said vector encoding said peptide fragment;
    culturing said transformed yeast and human cells, wherein a decrease in viability of said yeast cells compared to said human cells indicates that said peptide fragment is an inhibitor of fungal cell growth but not human cell growth; and
    adding said peptide fragment to a yeast cell culture, wherein a decrease in cell growth indicates that said peptide inhibits yeast, but not human, cell growth.

20. The method of claim 19, further comprising the step of contacting a desired fungus with said peptide fragment to confirm that said peptide fragment inhibits fungal, but not human, cell growth.

21. The method of claim 20, additionally comprising subjecting said vector to mutagenesis prior to the transforming steps.

22. The method of claim 20, wherein said Lys-147, Cys-149, Lys-151 and Glu-152 are chemically modified.

23. The method of claim 20, wherein said yTFIIB fragment contains glycine at position 115, asparagine at position 117 and arginine at position 182.

24. The method of claim 19, wherein said fungus is a pathogenic or nonpathogenic yeast strain.

25. The method of claim 24, wherein said pathogenic yeast strain is *Candida albicans*.

* * * * *

UNITED STATES PATENT AND TRADEMARK OFFICE
CERTIFICATE OF CORRECTION

PATENT NO. : 5,908,748
DATED : June 01, 1999
INVENTOR(S) : Ma et al.

It is certified that error appears in the above-identified patent and that said Letters Patent is hereby corrected as shown below:

Column 16, Line 45 after "peptide", please insert --fragment--.

Signed and Sealed this

Seventh Day of December, 1999

Attest:

Q. TODD DICKINSON

Attesting Officer

Acting Commissioner of Patents and Trademarks